United States Patent [19]
Singh et al.

[11] Patent Number: 6,136,378
[45] Date of Patent: Oct. 24, 2000

[54] METHOD OF COATING A SUBSTRATE USING CURABLE COMPOSITIONS CONTAINING NOVEL POLYFUNCTIONAL CROSSLINKING AGENTS

[75] Inventors: Balwant Singh, Stamford; Laurence Wu-Kwang Chang, New Haven, both of Conn.

[73] Assignee: Cytec Technology Corp., Wilmington, Del.

[21] Appl. No.: 09/432,746

[22] Filed: Nov. 3, 1999

Related U.S. Application Data

[62] Division of application No. 08/881,780, Jun. 24, 1997, Pat. No. 6,028,141
[60] Provisional application No. 60/020,353, Jun. 24, 1996.

[51] Int. Cl.[7] ........................................................ B02D 3/02
[52] U.S. Cl. ............................................................. 427/385.5
[58] Field of Search ...................... 427/385.5; 525/54.24, 525/58, 59, 61, 281, 437, 445, 453, 455, 523, 530, 532, 540; 528/289, 341, 367, 424

[56] References Cited

U.S. PATENT DOCUMENTS

| | | | |
|---|---|---|---|
| 4,138,398 | 2/1979 | Richter | 528/45 |
| 4,766,221 | 8/1988 | Floyd | 548/320 |

*Primary Examiner*—Patricia A. Short
*Attorney, Agent, or Firm*—Valerie T. Didamo

[57] ABSTRACT

Novel polyfunctional glyoxylated compounds and compositions containing the same are disclosed which are particularly suitable for use as crosslinking components in curable compositions and also find use in imparting wet adhesion properties to water-based paints and coatings. A process for preparing novel polyfunctional glyoxylated compounds is also disclosed.

2 Claims, No Drawings

METHOD OF COATING A SUBSTRATE USING CURABLE COMPOSITIONS CONTAINING NOVEL POLYFUNCTIONAL CROSSLINKING AGENTS

This application is a divisional of U.S. application Ser. No. 08/881,780, filed Jun. 24, 1997, now U.S. Pat. No. 6,028,141 which is incorporated by reference herein for all purposes as if fully set forth and which claims priority under 35 U.S.C. §119 from U.S. Provisional Application Serial No. 60/020,353 (filed Jun. 24, 1996), which is incorporated by reference herein as if fully set forth.

BACKGROUND OF THE INVENTION

1. Field of the Invention

This invention relates to novel ureido polyfunctional compounds and compositions which are particularly suitable as crosslinking components in curable compositions as well as for imparting wet adhesion properties to water based paints and coatings. Specifically, the novel ureido polyfunctional compounds of the present invention are useful in crosslinking water-soluble polymers.

2. Background

Crosslinked materials have found widespread use in coatings such as powder coatings, solution coatings, coil coatings, can coatings, and in non-coatings applications such as conventional moldings, reactive injection moldings, composites, water-soluble polymers, adhesives and in binders, paper and textile applications. Because crosslinked materials find applications in such widely different, increasingly diverse, and highly specialized areas, each such application has placed a new and usually unmet demand on the crosslinkers currently available or in use. There exists, therefore, a continuing need for new crosslinkers which are capable of meeting the requirements of a particular application.

We have now discovered a new class of ureido polyfunctional polyacylimidazolidinone compounds, i.e., polyfunctional glyoxylated maleurates, fumaurates, citraconurates, itaconurates and their related amido derivatives which function as external crosslinkers and which are capable of meeting the demands that have often not been met by existing crosslinkers. The present invention's novel polyfunctional glyoxylated maleurates, fumaurates, citraconurates, itaconurates and their related amido derivatives are also referred to herein as poly-glycomaleurates, polyglycomaleurates, polyglycocitraconurates, polyglycocitraconurates, polyglycomaleuramides, polyglycofumauramides, polyglycocitraconuramides and polyglycoitaconuramides. Specifically, the present invention's novel polyfunctional compounds are useful in curable compositions containing active hydrogen-containing polyfunctional materials and in forming aqueous emulsion polymers for crosslinked coating surfaces. This new class of polyfunctional compounds also surprisingly conveys wet adhesion properties to aqueous emulsion copolymer latices. Advantageously, the polyfunctional compounds of the present invention can also crosslink via free radical initiated processes which allows for their use in crosslinking unsaturated polymers.

SUMMARY OF THE INVENTION

As indicated above, the present invention is directed to novel polyfunctional glyoxylated compounds, specifically, poly-glycomaleurates, glycofumaurates, glycocitraconurates, glycoitaconurates and their related amido derivatives of the general Formula I below:

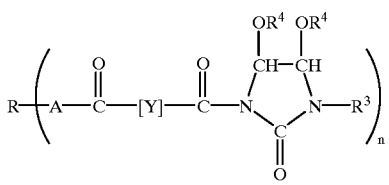

wherein n is a whole positive integer of at least 2;
wherein Y is

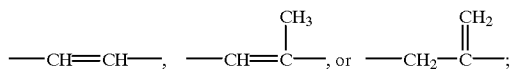

wherein A is —NH— or —O—;
wherein R is the residue of a poly(active hydrogen group)-containing compound after abstraction of n active hydrogen-containing groups, wherein the active hydrogen groups are selected from hydroxyl and amino groups;
wherein $R^3$ is hydrogen, an alkyl group having from 1 to 4 carbon atoms, a hydroxymethyl group, or an alkoxymethyl group having 2 to 4 carbon atoms in the alkoxy; and
wherein each $R^4$ is, individually, H or an alkyl group having from 1 to 6 carbon atoms.

Both the cis- and trans-stereoisomers of the above compounds, where appropriate (e.g., maleic and fumaric), are included within the above definition. It is also within the scope of the invention to use mixtures of the polyfuncfional compounds herein disclosed in compositions.

It is a further object of this invention to provide economically obtainable versatile polyfunctional compounds which are adaptable for use in widely varying circumstances, such as crosslinkers in curable compositions, as additives to improve corrosion and wet adhesion performance of coatings and paints, especially water-based paints, and as crosslinkers for textile, paper and wood finishing.

Accordingly, the invention further includes compositions comprising the polyfunctional compounds of the Formula (I), especially acrylic, vinyl and vinyl-acrylic latex paint compositions. The invention also includes curable compositions comprising: (a) a crosslinker component comprising the compound of the Formula I; and (b) active hydrogen-containing polyfunctional materials.

The present invention also relates to coating compositions based upon the above curable compositions, methods for coating substrates with such coating compositions, substrates so coated therewith, crosslinked films or objects derived from the curable compositions, and various other end uses thereof.

In addition, the present invention provides a method of enhancing the wet adhesion of aqueous polymer systems by incorporating the compounds of the present invention in aqueous polymer systems.

These and other features and advantages of the present invention will be more readily understood by those skilled in the relevant art from a reading of the following detailed description.

DETAILED DESCRIPTION OF THE PREFERRED EMBODIMENTS

Process for Preparing the Compounds of the Formula I

The compounds of the Formula I indicated above may be derived from such known compounds as N-carbamylmaleimide (NCMl), N-carbamylcitraconimide (NCCl) and N-carbamylitaconimide (NCll), which compounds have the Formulae indicated below:

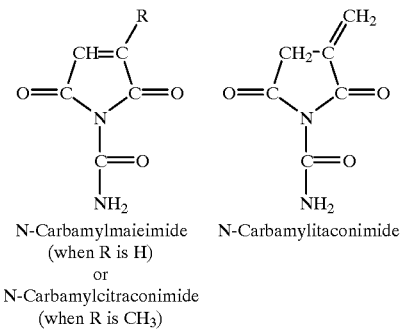

N-Carbamylmaieimide (when R is H) or N-Carbamylcitraconimide (when R is CH₃)

N-Carbamylitaconimide

The resulting novel compounds of the Formula (I) of the present invention which are derived from the above-described compounds are novel poly-glycomaleurates, glycofumaurates, glycocitraconurates, glycoitaconurates and their related amido derivatives.

In the preparation of the novel compounds, NCMl, NCCl or NCll is reacted with a poly (active hydrogen group)-containing compound to form polymaleurates, polycitraconurates, polyitaconurates, polymaleuramides, polycitraconuramides or polyitaconuramides, or polymaleurate/amides, polycitraconurates/amides, etc., under conditions known to skilled in the art. By poly (active hydrogen group)-containing compound is meant a compound containing at least two groups with active hydrogens, the groups being selected from one or a combination of hydroxyl and amino groups. The compound can be monomeric, oligomeric or polymeric in nature and fall within this definition so long as the compound contains at least two of hydroxyl and/or amino groups. The preferred polyfunctional coreactants are hydroxylfunctional and aminofunctional materials, with hydroxylfunctional materials being especially preferred. More preferred are the low molecular weight monomeric polyhydroxyl compounds.

The trans isomers of, for example, the polymaleurates and polymaleuramides, that is, polyfumaurates and polyfumauramides are formed by isomerization of the cis isomers by heating in the presence of low levels of isomerizing catalysts such as pyridine or AlCl₃ under conditions well known to those skilled in the art. The conversion of polyhydroxyl, polyamino or polyamino hydroxyl coreactants to polymaleurates, polycitraconurates, polyitaconurates, etc., is preferably carried out in a non-reactive organic solvent such as acetonitrile. Other suitable solvents include dimethylformamide, dimethylacetamide, dimethyl sulfoxide, dimethoxyethane. Acetonitrile is especially preferred particularly with di- and trihydroxy reactants.

As examples of monomeric hydroxyl groups-containing compounds meeting the above definition may be mentioned the polyhydric alcohols, e.g., ethylene glycol, propylene glycol, 1,4-butanediol, 1,6-hexanediol, dimethylol cyclohexane, hydroxy terminated polybutadienes, glycerol, trimethylolpropane, pentaerythritol, monoglycerides, diglycerides, triglycerides containing one or more alcoholic hydroxyl groups, e.g., castor oil, and "blown" linseed oil, methylol phenols, e.g., 2,6-dimethylol-4-alkyl-phenols and their condensation polymers, N-methylol compounds, e.g., N-methylolmaleimide and N,N'-dimethylolurea, and alcohols containing sulfone groups, e.g., those alcohols made from a glycol and divinyl sulfone.

As examples of monomeric amino groups-containing compounds (primary and secondary amino groups) meeting the above definition may be mentioned ethylenediamine, propylenediamine, 1,4-diaminobutane, hexamethylene diamine, aromatic diamines such as 4,4'-diaminodiphenylmethane, toluene diamine, isophorone diamine, diaminocyclohexanes, α,α,α',α'-tetramethylxylylene diamines, diethylenetriamine, triethylenetetramine, and the like.

As examples of monomeric compounds containing both hydroxyl and amino groups may be mentioned ethanolamine, diethanolamine, triethanolamine, propanolamines, butanolamines, and the like.

As examples of oligomeric/polymeric compounds containing hydroxyl groups may be mentioned polyethylene glycols, polypropylene glycols, hydroxyfunctional low-molecular weight polyacrylate resins, polyvinyl alcohol and partial ethers and esters thereof, hydroxyfunctional polyesters, and the like.

As examples of oligomeric/polymeric compounds containing amino groups may be mentioned polyvinylamine, polyallylamine, polyethyleneimine, polypropylenelmine, and the like.

As examples of oligomeric/polymeric compounds containing boththydroxyl and amino groups may be mentioned aminated starches and cellulosics.

The polymaleurates, polycitraconurates, polyitaconurates, polymaleuramides, polymaleurate/amides, etc., formed above, are then reacted with aqueous glyoxal and heated under refluxing conditions including, for example, refluxing water or dioxane or mixtures of the two resulting in polyglycomaleurates, polyglycocitraconurates, polymaleurate/amides, etc. The preferred pH range for the reaction is 7.0–7.5, thus the pH of commercial glyoxal is adjusted to 7.0–7.5 with aqueous sodium bicarbonate prior to such reaction. The glyoxylation reaction may result in partial or complete glyoxylation of the polymaleurates, polycitraconurates, polyltaconurates, polymaleuramldes, etc., depending on the number of maleurate, citraconurate, itaconurate, etc. functionalites. Specifically the glyoxylation reaction may or may not convert all urea groups to their corresponding dihydroxyimidazolidinone groups. As a result, the products may have both urea and dihydroxyimidazolidinone functionalities, in addition to some residual hydroxyl or amino groups from the first step.

The trans isomers, that is, for example, polyglycofumaurates, polyglycofumauramides and polyglycofumaurate/amides are similarly prepared by first isomerizing the polymaleurate, polymaleuramide or polyfumaurate/amide to the polyfumaurate, polyfumaramide, polyfumaurate/amide, etc., followed by glyoxylation with aqueous glyoxal as indicated above. The isomerization is conducted by heating the polymaleurate, etc., in the presence of catalysts including, for example, hydrochloric and sulfuric acids, AlCl₃ and pyridine, etc., preferably in a solvent such as acetonitrile.

A preferred one-pot process for making the polyglycomaleurate, polyglycocitraconurate, polyglycoitaconurate, polyglycomaleuramide, etc. compounds of the present invention comprises (1) reacting urea and maleic, citraconic or itaconic anhydride in a non-reactive polar organic solvent, including, for example, acetone, acetonitrile, methyl ethylketone and acetic acid, at a temperature range of 50°–100° C., preferably 60° to 80° C., for 4–10 hours to form maleuric, citraconuric or itaconuric acid. The preferred solvents, include acetic and acetonitrile, with acetic acid being especially preferred; (2) adding a dehydrating agent, including, for example, acetic anhydride, proprionic anhydride and butyric anhydride to the reaction mixture and heating at a temperature range indicated in step (1), above, for an additional 2 to 4 hours to form N-carbamylmaleimide, N-carbamylcitraconimide or N-carbamylitaconimide; (3) adding a polyhydroxy, polyamino or polyaminohydroxy coreactant and heating for 3 to 6 hours at the same temperature range indicated above to form the polymaleurate, polycitraconurate, polyitaconurate, the related amido derivatives or the related hydroxy/amido derivatives; (4) removing the non-reactive polar organic solvent (i.e., acetic acid) under reduced pressure to form a residue, and (5) reacting the residue with aqueous glyoxal in the pH range of 7.0–7.5 under refluxing conditions to form the polyglycomaleurates, is CH═CH, A is O and R is derived from a polyhydroxyl coreactant. More preferred are crosslinkers where the hydroxylfunctional coreactant is a low molecular weight diol, triol or an aminoalcohol. By way of example, the reaction of ethylene glycol with NCM1 produces the bis-maleurate which on further reaction with glyoxal yields the novel bis-dihydroxyimidazolidinone crosslinker, I, below. The reaction of trimethylolpropane with NCM1 produces a mixture of bis and tris urea derivatives which on further reaction with glyoxal produces a mixture of bis and tris-dihydroxyimidazolidinones, II, below. The chemical compositions of these crosslinkers are shown below.

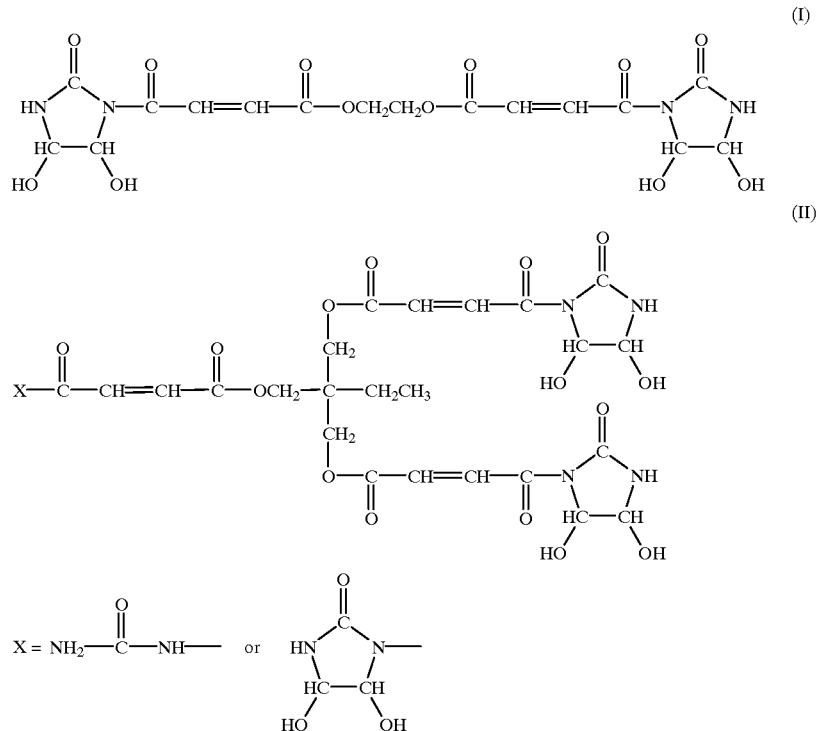

polyglycocitraconurates, polyglycocitraconurates, etc. The refluxing conditions include heating under refluxing water, refluxing dioxane or refluxing mixtures thereof and is well known to those skilled in the art.

The Polyfunctional Glyoxylated Crosslinking Agent

The novel polyfunctional compounds of the present invention are polyfunctional glyoxylated crosslinking agents as represented by the general Formula (I), above. In the Formula I, R is an anchor group which is derived from a polyfunctional active hydrogen-containing material. Specifically, R is the residue of a poly (active hydrogen group)-containing compound after abstraction of a certain number of active hydrogens, which residue is obtained by the reaction of NCMl, NCCl or NCll with a polyhydroxyl and/or polyamino compound. The number of active hydrogens abstracted depends on the conversion and the number of moles NMCl, NCCl or NCll used and the number of active hydrogen groups on the polyactive hydrogen-containing material.

A preferred embodiment for the present invention are those compounds represented by the Formula I, wherein Y Uses of the Novel Polyfunctional Compounds The novel polyfunctional compounds of the present invention contain reactive olefinic as well as dihydroxy/alkoxy acyl imidazolidinone functionalities. These materials can therefore crosslink through olefinic as well as the dihydroxy/alkoxy acyl imidazolidinone moieties.

The novel compounds are suitable for use in curable compositions containing active hydrogen-containing polyfunctional materials. For example, they can be used as crosslinkers either in solution or emulsion form, incoatings, binders or, adhesive compositions for a variety of substrates. They are also useful in textile, paper and wood finishes as well as corrosion inhibitors, insolubilizers for starch, formaldehyde scavengers, pigment modifiers and components of primers. They may be used as crosslinkers during homo and copolymerizations of water-soluble monomers such as acrylamide, methacrylamide, N-vinylformamide, N-vinylacetamide and the like. The crosslinking reactions are readily carried out by the use of radical Initiators well known to those skilled in the art. The novel polyfunctional compounds may also be post-added to latex and primer formulations to improve adhesion.

In particular, the novel polyfunctional compounds are especially suited for use as crosslinkers in water-based systems. They may be used in aqueous emulsion polymer systems, including in compositions comprising such monomers as methyl acrylate, ethyl acrylate, methyl methacrylate, butyl acrylate, 2-ethylhexyl acrylate, other acrylates, methacrylates and their blends, styrene, vinyltoluene, vinyl acetate, vinyl esters of higher carboxylic acids than acetic acid, acrylonitrile, acrylamide, vinyl chloride and the like, and mixtures thereof. They may also be added as "post-adds" to finished polymer systems and/or primer formulations.

Accordingly, this invention is also directed to compositions comprising the novel polyfunctional compounds of the present invention, polymers made therefrom and compositions, especially acrylic and vinyl/acrylic latex paints comprising polymers made from the polyfunctional compounds of the present invention.

In particular, the polyfunctional compounds of this invention may be incorporated in effective amounts in aqueous polymer systems to enhance the wet adhesion of paints made from the polymers. The commonly used ethylenically unsaturated monomers in making acrylic paints are butyl acrylate, methyl methacrylate, ethyl acrylate and mixtures thereof. In acrylic paint compositions at least 50% of the polymer formed is comprised of an ester of acrylic or methacrylic acid. The vinyl-acrylic paints usually include ethylenically unsaturated monomers such as vinyl acetate and butyl acrylate or 2-ethylhexyl acrylate. In vinyl-acrylic paint compositions, at least 50% of the polymer formed is comprised of vinyl acetate, with the remainder being selected from the esters of acrylic or methacrylic acid.

The polyfunctional compounds of this invention may be added to the monomer composition from which acrylic or vinyl-acrylic polymers are formed in a concentration which may vary over a wide range. Preferably the concentration is at least sufficient to improve the wet adhesion of paints made from the polymer composition. Concentrations may range from about 0.1% to about 20%, by weight, based on the total weight of the monomers. Preferably, the concentration is in the range of from about 0.2% to about 5%, and more preferably from about 0.5% to about 1.5%, same basis.

When used as vinyl polymerizable crosslinkers in latex applications, the polymerization of the media which includes ethylenically unsaturated monomers and the novel polyfunctional compounds of the present invention can be accomplished by known procedures for polymerization in aqueous emulsions. Other ingredients, such as various free radical catalysts to initiate polymerization, surfactants with or without colloids to protect particles from agglomeration, and buffers to maintain a desired pH during polymerization, as are generally well-known to those of ordinary skill in the art of polymerization may also be employed.

Curable Compositions

An important use of the compounds described herein is based on their ability to act as crosslinking agents in curable compositions, and especially those curable compositions which contain materials which have active hydrogen groups. The crosslinkers have at least two reactive sites which are capable of crosslinking active hydrogen containing resins, for example.

The polyfunctional material containing a functionality capable of reacting with the polyfunctional glyoxylated crosslinkers of the invention under normal coatings cure conditions (generally between about 25° C. to about 250° C.) are well known backbone resins widely used in amino resin crosslinked coatings. These resins contain at least two (2) reactive functionalities each preferably independently selected from the group consisting of hydroxy, carboxy, amino, amido, carbamato functionalities and a group convertible thereto. These polyfunctional materials are those which are conventionally used in coatings and in general are considered well-known to those of ordinary skill in the art. The preferred polyfunctional materials which are reactive with the polyfunctional crosslinker of the present invention are polyhydroxyfunctional materials.

Especially suitable active hydrogen-containing materials, wherein the active hydrogen functionality is hydroxy, include acrylic resins, polyester resins, polyurethanes, polyols, products of condensation of epoxy resins with amines, and mixtures thereof. The preparation of polyesters, polyacrylates and polyurethanes is well known to those skilled in the art. Other suitable hydroxyl functional resins will be readily understood by those of ordinary skill in the art.

For example, it is known to those skilled in the relevant art that polyesters may be obtained by the reaction of polycarboxylic acids with excess quantities of polyhydric alcohols. It is also known that polyacrylates may be obtained by the copolymerization of acrylic or methacrylic acid derivatives with hydroxy group-containing derivatives of these acids, such as, for example, the hydroxyalkylesters, optionally with the simultaneous use of additional vinyl compounds, such as, for example, styrene. Additionally, it is known that the hydroxy group-containing polyurethanes can be prepared by the reaction of polyisocyanates with excess quantities of compounds containing at least two hydroxy groups.

Suitable polyfunctional active hydrogen-coating materials, wherein the active hydrogen functionality is amino include, for example, diamines, triamines, polyamines and mixtures thereof.

The curable compositions of the present invention may optionally further comprise a curing catalyst which is, in general, well known to those of ordinary skill in the art, however the polyfunctional crosslinker of the present invention is capable of curing without the aid of an added catalyst. When a curing catalyst is present, the crosslinking takes place more rapidly at a particular temperature than when a catalyst is not present. Typically, crosslinking is effected at a lower temperature with a catalyst present.

The curing catalysts usable in the present invention include sulfonic acids, aryl, alkyl and aralkyl acid phosphates, aryl, alkyl, and aralkyl acid pyrophosphates, carboxylic acids, sulfonimides, mineral acids and a mixture thereof. Of the above acids, sulfonic acids are preferred when a catalyst is utilized. Examples of the sulfonic acids include benzenesulfonic acid, para-toluene sulfonic acid, dodecylbenzenesulfonic acid, naphthalenesulfonic acid, dinoylnaphthalenedisulfonic acid, mixtures thereof and the like. Examples of the aryl, alkyl, and aralkyl phosphates and pyrophosphates include phenyl, para-tolyl, methyl, benzyl, diphenyl, di-para-tolyl, di-methyl, di-ethyl, di-benzyl, phenyl-para-tolyl, methyl-ethyl, phenyl-benzyl phosphates and pyrophosphates, etc. Examples of the carboxylic acids include benzoic acid, formic acid, acetic acid, propionic acid, butyric acid, and the like. Examples of the sulfonimides include dibenzene sulfonimide, di-para-toluene sulfonimide, methyl-para-toluene sulfonimide, dimethyl sulfonimide, and the like. Examples of the mineral acids include nitric acid, sulfuric acid, phosphoric acid, polyphosphoric acid, and the like. Other suitable catalysts include ammonium sulfate and ammonium chloride, which are particularly useful for textile applications.

The curable composition may also contain other optional ingredients such as fillers, light stabilizers, pigments, flow control agents, plasticizers, mold release agents, corrosion inhibitors, and the like. It may also contain, as an optional ingredient, a medium, such as a liquid medium, to aid the uniform application and transport of the curable composition. Any or all of the ingredients of the curable composition may be contacted with the liquid medium. Moreover, the liquid medium may permit formation of a dispersion, emulsion, inverse emulsion, or solution of the ingredients of the curable composition. Particularly preferred is a liquid medium which is a solvent for the curable composition ingredients. Suitable solvents include aromatic hydrocarbons, aliphatic hydrocarbons, halogenated hydrocarbons, ketones, esters, ethers, amides, alcohols, water, compounds having a plurality of functional groups such as those having an ether and an ester group, and a mixture thereof.

The relative amounts of the components in accordance with the present invention are not in general critical. Any proportion of ingredients may be employed that results in a curable coating composition capable of providing a durable, substantially surface defect-free finish after curing. In general, the ratio of the polyfunctional material to the glyoxylated crosslinking agent of the present invention is in the range of from about 99:1 to about 0.5:1. Preferably the amount of glyoxylated crosslinker employed is in the range of from about 3.0 to about 50.0 wt %, and more preferably in the range of from about 10.0 to about 30.0 wt %, of the combined weight of the crosslinker of the present invention and the polyfunctional material (backbone resin) being cross-linked. Conversely, the preferred amount of the polyfunctional material containing a functionality capable of reacting with the glyoxylated crosslinker of the present invention is typically in the range of from about 70.0 to about 97.0 wt %, and more preferably in the range of from about 80.0 to about 85.0 wt % of the combined weight of the present invention's crosslinker and the polyfunctional material. The weight percent of the cure catalyst, if present, is generally in the range of from about 0.01 to about 5.0 wt % based upon the combined weight of the backbone resin and crosslinker.

An important use of the above-described curable compositions is in the formulation of coating compositions especially for water borne systems. The present invention is accordingly also directed to coating compositions as well as to methods of coating substrates by applying onto a substrate the coating compositions and heat curing the same. In the method of coating, a free radical initiator may be used, as known to those of ordinary skill in the art.

The present coating compositions may employ a liquid medium such as water, or it may employ solid ingredients as in powder coatings which typically contain no liquids. Low melting solids (M.P.: 70°–110° C.) are particularly preferred. Contacting may be carried out by dipping, spraying, padding, brushing, rollercoating, flowcoating, curtaincoating, electrocoating or electrostatic spraying.

The liquid or powder coating compositions and a substrate to be coated are contacted by applying the curable composition containing the novel crosslinkers of the instant invention onto the substrate by a suitable method, for example, by spraying in the case of the liquid compositions and by electrostatic spraying in the case of the powder compositions. In the case of powder coatings, the substrate covered with the powder composition is heated to at least the fusion temperature of the curable composition forcing it to melt and flow out and form a uniform coating on the substrate. It is thereafter fully cured by further application of heat, typically at a temperature in the range of about 120° C. to about 220° C. for a period of time in the range of about 5 minutes to about 30 minutes and preferably for a period of time in the range of about 10 to about 20 minutes. In the case of the liquid compositions, the solvent is allowed to partially evaporate to produce a uniform coating on the substrate. Thereafter, the coated substrate is heated in an oven at a temperature up to about 250° C., for a period of time in the range of about 20 seconds to about 14 days and preferably for a period of time in the range of 10 to 45 minutes to obtain a fully cured film.

Uses of the Curable Compositions

The heat cured compositions of this invention may be employed as coatings in the general areas of coatings such as original equipment manufacturing (OEM) including automotive coatings, general industrial coatings, including industrial maintenance coatings, architectural coatings, powder coatings, coil coatings, can coatings, wood coatings, and low temperature cure automotive refinish coatings. They are usable as coatings for wire, appliances, automotive parts, furniture, pipes machinery, and the like. Suitable surfaces include metals such as steel and aluminum, plastics, wood, and glass. The polyfunctional crosslinkers of the present invention are also well suited for use in compositions used to refinish automotive parts and to coat sensitive substrates such as wood.

The polyfunctional crosslinkers of the present invention may also be used in compositions used as binders for nonwovens, as textile treatment agents for permanent press textiles, as coating insolubilizers for gellation of starch in paper and as colloidal wet and dry strength agents in paper manufacture. In addition to coatings, curable compositions containing the crosslinkers of the present invention may be used in adhesives, paper, textile, decorative laminated boards and crosslinked molded articles. They may also be used as corrosion inhibitors, formaldehyde scavengers and as additives to primer formulations.

The examples which follow are intended to be illustrative of certain preferred embodiments of the invention and are not to be construed to limit the invention in any manner.

EXAMPLE A

Trimethylolpropane trimaleurate

A mixture of 9.86 g of trimethylolpropane (0.074 moles), 31.3 g of N-carbamylmaleimide (0.224 moles) and 0.85 g of zinc chloride (0.00625 moles) in 215 mL of acetonitrile was heated to reflux. After 5 hours, the acetonitrile was evaporated to afford 40.7 g of trimethylolpropane trimaleurate as a white solid. M.P.: 70°–76° C.; $^1$H NMR (DMSO-$d_6$): δ 10.5 (s, 3 H), 7.2–7.7 (m, 6 H), 6.3–6.6 (m, 6 H), 4.1 (s, 6 H), 1.35 (q, 2 H), 1.85 (t, 3 H).

EXAMPLE 1

Glyoxylated trimethylolpropane trimaleurate

The pH of 9.4 g of 40% glyoxal (0.065 moles) was adjusted to 7.1 with aqueous saturated sodium bicarbonate. 12 g of trimethylolpropane trimaleurate (0.022 moles) and 43 mL of $H_2O$ were added and the mixture was heated to 95° C. After 4 hours, the $H_2O$ was evaporated to afford 17.2 9 of a light tan solid. M.P.: 65°–71° C.

EXAMPLE B

Ethylene glycol bismaleurate

A mixture of 3 g of ethylene glycol (0.048 moles), 12 g of N-carbamylmaleimide (0.086 moles) and 0.3 g of zinc chloride (0.0022 moles) in 70 mL of acetonitrile was heated to reflux. After 3 hours, a lot of solid material had been produced from the mixture. The mixture was filtered and the solids washed with acetonitrile and dried to afford 11.7 g of ethylene glycol bismaleurate. M.P.: 158°–60° C.; $^1$H NMR (DMSO-d$_6$): δ 10.5 (s, 2 H), 7.2–7.8 (m, 4 H), 6.2–6.4 (m, 4 H), 4.3 (s, 4 H).

EXAMPLE 2

Glyoxalated ethylene glycol bismaleurate

The addition of glyoxal to ethylene glycol bismaleurate under the conditions of Example 1 afforded 9.3 g of the addition product as a yellow-orange semi-solid.

EXAMPLE C 1,6-Hexanediol bismaleurate

A mixture of 5.66 g of 1,6-hexanediol (0.048 moles), 12 g of N-carbamylmaleimide (0.086 moles) and 0.3 g of zinc chloride (0.0022 moles) in 70 mL of acetonitrile was heated to reflux. After 3 hours, a lot of solid material had been produced from the mixture. The mixture was filtered and the solids washed with acetonitrile and dried to afford 12.1 g of 1,6-hexanediol bismaleurate.

EXAMPLE 3

Glyoxalated 1,6-hexanediol bismaleurate

The addition of glyoxal to ethylene glycol bismaleurate under the conditions of Example 1 afforded 10.2 g of the addition product.

EXAMPLE D

Polypropylene glycol bismaleurate

A mixture of 20.4 g of polypropylene glycol (hydroxyl number 263, avg M$_w$=425, 0.048 moles), 12 g of N-carbamylmaleimide (0.086 moles) and 0.3 g of zinc chloride (0.0022 moles) in 70 mL of acetonitrile was heated to reflux. After 3 hours, a lot of solid material had been produced from the mixture. The mixture was filtered and the solids washed with acetonitrile and dried to afford 30 g. of polypropylene glycol bismaleurate.

EXAMPLE 4

Glyoxylated polypropylene glycol bismaleurate

The addition of glyoxal to polypropylene glycol bismaleurate under the conditions of Example 1 afforded 17.8 g of the addition product.

EXAMPLE 5

Crosslinking of Polyvinyl Alcohol

A formulation containing 5 g of 10% aqueous polyvinyl alcohol (80% hydrolyzed, average M$_w$ 9,000–10,000) and 0.4 g of glyoxalated trimethylolpropane trimaleurate was placed on a stainless steel plate and heated at 140° C. for 20 minutes. A thin film was obtained. The film showed excellent chemical (MEK double wiple >200) and water (water double wipe >200) resistance properties. A formulation of aqueous polyvinyl alcohol, trimethylolpropane trimaleurate, and p toluenesulfonic acid catalyst could not be cured under the same conditions.

Although the present invention is described with reference to certain preferred embodiments, it is apparent that variations or modifications thereof may be made by those skilled in the art without departing from the scope of this invention as defined by the appended claims.

What is claimed is:

1. A method of coating a substrate by (1) applying a coating composition comprising:

(a) a crosslinker component comprising a polyfunctional glyoxylated compound of the Formula I

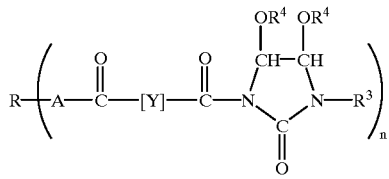

wherein n is a whole positive integer of at least 2;
wherein Y is

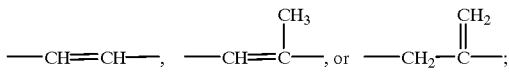

wherein A is —NH— or —O—;
wherein R is the residue of a poly (active hydrogen group)-containing compound after abstraction of n active hydrogen-containing groups, wherein the active hydrogen groups are selected from hydroxyl, amino and aminohydroxyl groups;
wherein R$^3$ is hydrogen, an alkyl group having from 1 to 4 carbon atoms, a hydroxymethyl or an alkoxymethyl group having 2 to 4 carbon atoms; and
wherein each R$^4$ is H or an alkyl group having from 1 to 6 carbon atoms; and (b) a polyfunctional active hydrogen-containing material containing on average of at least two groups with active hydrogen functionality and/or functionality convertible thereto; and (2) heat curing the so-applied coating.

2. The method of claim 1 further comprising an effective amount of a free radical initiator.

* * * * *